US011089945B2

(12) United States Patent
Eisenkolb et al.

(10) Patent No.: US 11,089,945 B2
(45) Date of Patent: Aug. 17, 2021

(54) OBSERVATION INSTRUMENT FOR ACCURATE POSITIONING OF OPTICAL COMPONENTS

(71) Applicant: Karl Storz SE & Co. KG, Tuttlingen (DE)

(72) Inventors: Peter Eisenkolb, Tuttlingen (DE); Johannes Eisenlauer, Tuttlingen (DE); Stefanie Maichle, Tuttlingen (DE); Florian Wanner, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 446 days.

(21) Appl. No.: 15/940,035

(22) Filed: Mar. 29, 2018

(65) Prior Publication Data
US 2018/0279856 A1   Oct. 4, 2018

(30) Foreign Application Priority Data

Mar. 29, 2017   (DE) ......................... 102017106714.0

(51) Int. Cl.
| *A61B 1/00* | (2006.01) |
| *A61B 1/07* | (2006.01) |
| *A61B 90/70* | (2016.01) |
| *A61B 90/00* | (2016.01) |

(Continued)

(52) U.S. Cl.
CPC ........ *A61B 1/00096* (2013.01); *A61B 1/0008* (2013.01); *A61B 1/00078* (2013.01); *A61B 1/00128* (2013.01); *A61B 1/00188* (2013.01); *A61B 1/00195* (2013.01); *A61B 1/07* (2013.01); *A61B 1/002* (2013.01); *A61B 1/0011* (2013.01);

(Continued)

(58) Field of Classification Search
CPC combination set(s) only.
See application file for complete search history.

(56) References Cited

U.S. PATENT DOCUMENTS

| 4,738,255 A | * | 4/1988 | Goble ................ A61B 17/0401 |
| | | | 29/243.519 |
| 5,507,297 A | * | 4/1996 | Slater ..................... A61B 17/29 |
| | | | 600/564 |
| 5,601,525 A | | 2/1997 | Okada |

(Continued)

FOREIGN PATENT DOCUMENTS

| CN | 102736239 A | * 10/2012 | ......... G02B 23/2423 |
| DE | 1248224 B | 8/1967 | |

(Continued)

OTHER PUBLICATIONS

German Search Report Applicaiton No. DE 10 2017 106 714.0 dated Nov. 17, 2017 9 pages.

(Continued)

*Primary Examiner* — John P Leubecker
*Assistant Examiner* — Shankar Raj Ghimire
(74) *Attorney, Agent, or Firm* — Whitmyer IP Group LLC (57) ABSTRACT

An observation instrument comprises an instrument shaft having a distal end and a proximal end, and an optical arrangement extending at least sectionally through the instrument shaft. The optical arrangement comprises at least one optical component that is accommodated in a support shaft. The support shaft is arranged in the instrument shaft in an at least sectionally axially displaceable manner and is preloaded distally.

18 Claims, 6 Drawing Sheets

(51) Int. Cl.
*A61B 1/002* (2006.01)
*A61B 1/04* (2006.01)

(52) U.S. Cl.
CPC ....... *A61B 1/042* (2013.01); *A61B 2090/0813* (2016.02); *A61B 2090/701* (2016.02)

(56) References Cited

U.S. PATENT DOCUMENTS

| | | | | |
|---|---|---|---|---|
| 5,609,561 | A * | 3/1997 | Uehara | A61B 1/042 348/75 |
| 5,711,756 | A * | 1/1998 | Chikama | A61B 1/00096 600/112 |
| 5,980,450 | A * | 11/1999 | Thompson | A61B 1/00142 600/112 |
| 6,117,071 | A * | 9/2000 | Ito | A61B 1/00059 600/118 |
| 6,346,073 | B1 * | 2/2002 | Thompson | A61B 1/00142 600/112 |
| 6,346,076 | B1 * | 2/2002 | Rovegno | A61B 1/00177 600/137 |
| 6,419,628 | B1 * | 7/2002 | Rudischhauser | A61B 1/00135 600/130 |
| 6,425,857 | B1 * | 7/2002 | Rudischhauser | A61B 1/00195 600/112 |
| 6,471,640 | B1 | 10/2002 | Frische et al. | |
| 6,955,644 | B2 | 10/2005 | Forkey et al. | |
| 7,011,626 | B2 * | 3/2006 | Huber | A61B 1/00165 600/133 |
| 7,714,885 | B2 * | 5/2010 | Yazawa | A61B 1/00188 348/65 |
| 7,880,977 | B2 | 2/2011 | Lederer et al. | |
| 9,408,525 | B2 * | 8/2016 | Dahmen | A61B 1/00101 |
| 9,516,998 | B2 * | 12/2016 | Iwasaki | A61B 1/00188 |
| 2005/0192479 | A1 | 9/2005 | Forster et al. | |
| 2005/0261693 | A1 * | 11/2005 | Miller | A61B 17/3472 606/80 |
| 2006/0004378 | A1 * | 1/2006 | Raines, Jr. | A61F 2/4202 606/99 |
| 2007/0100209 | A1 * | 5/2007 | Takahashi | A61B 1/00096 600/167 |
| 2008/0212212 | A1 * | 9/2008 | Matsuki | A61B 1/00188 359/824 |
| 2012/0318110 | A1 * | 12/2012 | Lavelle | A61B 17/00234 81/489 |
| 2014/0128679 | A1 | 5/2014 | Wieters | |
| 2020/0360048 | A1 * | 11/2020 | White | A61B 1/233 |

FOREIGN PATENT DOCUMENTS

| | | |
|---|---|---|
| DE | 19912656 A1 | 11/2000 |
| DE | 10253559 A1 | 6/2004 |
| DE | 102010050932 A1 | 5/2012 |
| DE | 102011078968 A1 | 1/2013 |
| DE | 102016207275 A1 | 11/2017 |
| FR | 2317673 A1 | 2/1977 |
| WO | 9843529 A1 | 10/1998 |
| WO | 9939623 A1 | 8/1999 |

OTHER PUBLICATIONS

European Search Report Application No. EP18164491 Completed: Jul. 6, 2018 8 pages.

* cited by examiner

OBSERVATION INSTRUMENT FOR ACCURATE POSITIONING OF OPTICAL COMPONENTS

CROSS-REFERENCES TO RELATED APPLICATIONS

This application claims priority from German patent application 10 2017 106 714.0, filed on Mar. 29, 2017. The entire content of that priority application is fully incorporated by reference herewith.

BACKGROUND

The present disclosure relates to an observation instrument, which is provided with an instrument shaft having a distal end and a proximal end. Furthermore, the observation instrument comprises an optical arrangement at least partially extending through the instrument shaft. The optical arrangement comprises at least one optical component that is accommodated in a support shaft.

More specifically, the present disclosure relates to an endoscope. In certain embodiments, the present disclosure relates to an endoscope that is arranged for observing body cavities. Endoscopes of that kind are generally arranged for observations inside the body, which requires that at least a distal end of the endoscope is inserted through an opening into the body.

Observation instruments of the aforementioned type are generally known in the art. This may involve medical observation instruments, for example. However, observation instruments for technical applications and industrial applications, such as component inspection and diagnostic purposes are also conceivable. These devices may also be arranged as and referred to as endoscopes, but configured for non-medical or non-surgical purposes.

Observation instruments may be arranged as endoscopes. This may also involve observation instruments for specific applications, such as laparoscopy and other medical areas.

Endoscopes are regularly distinguished into rigid endoscopes and flexible endoscopes. Each type has specific features and characteristics. Flexible endoscopes regularly have a deflectable shaft arrangement, whereas optical fibers are regularly provided for transmitting the illumination light and/or the optical image.

The present disclosure relates in at least some exemplary embodiments to so-called rigid endoscopes having a rigid shaft arrangement. Optical components are regularly provided in the shaft arrangement to provide an optical image of an observed object at a proximal end of the shaft assembly and/or endoscope. The image can be displayed for an observer at an eyepiece. However, the image may also be formed in a sensor plane of an image sensor at the proximal end of the shaft assembly and/or the endoscope.

From US 2014/0128679 A1 there is known a side-view endoscope, the endoscope comprising a proximal handle, an endoscope shaft with an outer tube and an inner tube, two optical assemblies arranged in the distal region of the endoscope shaft, which are rotatable relative to each other about a longitudinal axis of the endoscope shaft and which are supported against each other by an axial bearing arranged between the optical assemblies and prestressed by means of a preloading device.

From U.S. Pat. No. 9,408,525 B2 and U.S. Pat. No. 6,471,640 B1, further designs of shaft arrangements for endoscopes are known.

From U.S. Pat. No. 7,880,977 B2 there is known an endoscope comprising a rod lens arrangement that is arranged between distal, object-side optics and proximal, eyepiece-side optics. Such an arrangement may also be referred to as a Hopkins rod lens system.

From U.S. Pat. No. 6,419,628 B1 there is known an endoscope having an outer tube and an inner tube, wherein an optical arrangement is accommodated in the inner tube, comprising an objective lens assembly, an ocular assembly and an intermediate rod lens assembly. The inner tube is at its distal end fixedly attached to the outer tube. The outer tube is mounted at its proximal end to a head that serves as housing. A spring is provided between the ocular assembly and the rod lens assembly, which pretensions the rod lens assembly distally.

From U.S. Pat. No. 6,955,644 B2 there is known an endoscope which comprises a shaft assembly comprising an outer tube, an inner tube and an inner shaft. The inner tube is accommodated in the outer tube. Optical fibers are arranged in an intermediate space between the outer tube and the inner tube. The inner shaft is arranged in the inner tube. The inner shaft is sealed to the outside and accommodates sensitive optical components. The inner shaft is at its distal end firmly attached to the inner tube. The inner shaft accommodates optical components that are pretensioned distally by a spring, which is supported at a proximal end of the inner shaft.

In the context of the present disclosure, the term "proximal" describes an area or portion of a unit or component which is facing away from the object to be observed and facing an observer or user of the observation instrument. Accordingly, the term "distal" describes an area facing the object to be observed and facing away from the observer or user of the observation instrument. In a medical endoscope that is arranged for insertion into body openings, the distal end of the instrument shaft is regularly inserted into the body. The proximal end of the instrument shaft or the observation instrument, however, remains outside the body.

The instrument shaft of an observation instrument regularly comprises a considerable longitudinal extension, i. e. a large length-to-diameter ratio. In general, it is desirable to design the instrument shaft with the smallest possible diameter. This may involve designs that—depending on the field of application—encompass a shaft diameter of the instrument shaft in the range of 12 mm to 10 mm, to a diameter in the range of 8 mm to 6 mm or even in the range of 5 mm to 4 mm. In this way, in the case of a medical application, it is possible to observe the inside of a patient's body with only small body openings required to insert the observation instrument. Similarly, technical applications also benefit from the use of instrument shafts with a small diameter.

The optical arrangement of an observation instrument generally comprises optical components which, depending on their position in relation to or between an object to be observed and/or an observer, may be associated with or arranged at a lens assembly or an ocular assembly. Further arrangements are conceivable. A certain type of observation instrument further involves a rod lens arrangement between an objective lens assembly and an ocular assembly of an optical arrangement. The rod lens arrangement may include, for example, a so-called Hopkins lens system.

The term ocular assembly shall not be understood in a limiting sense to mean that the image is necessarily provided by the ocular assembly for direct observation by the human eye. Alternatively or in addition, it is conceivable to couple the ocular assembly with an image sensor, such as a CCD chip and/or a CMOS chip, in order to provide a digital image. Further, observation instruments are known, which can be converted for direct observation with the human eye and for the use of image sensors.

Generally, the use of rod lens systems allows a bright image reproduction. This may also contribute to a reduction of the diameter of the instrument shaft or an increase of the length-to-diameter ratio.

Further, observation instruments are known that comprise an inclined or lateral viewing direction that is angularly offset to a longitudinal axis of the instrument shaft. This may involve a fixed lateral view angle. Further, endoscopes are known that comprise variable viewing angles and that are provided, for this purpose, on the objective side with swivel prisms or similar arrangements.

To maintain the image quality, it is important to avoid contamination of the optical arrangement. This applies both to observation instruments for technical applications and for medical applications. In addition, medical observation instruments must be regularly cleaned and/or sterilized intensively in order to enable them to be used on the human or animal body. Usually, medical observation instruments, at least subassembly thereof, are regularly autoclaved. In this way, sterilization takes place.

On the one hand, the above-mentioned requirements require an adequate sealing of at least the optical arrangement, which usually also applies to other components of the observation instrument. Furthermore, boundary conditions and parameters of sterilization must be taken into account when designing observation instruments. On the one hand, this applies an increased temperature and, on the other hand, to an increased pressure and/or a certain moisture content, for instance in the context of a so-called steam pressure sterilization.

Furthermore, the minimization of installation space, for instance the minimization of diameters, must always be taken into account when designing observation instruments. A further challenge for the design and manufacture of observation instruments is a high-precision assembly and adjustment of the optical components involved. In this way, the desired image quality can be ensured.

In the context of designing optical observation instruments that are arranged as endoscopes, a design with several tubes arranged one inside the other has been prevailing. This may involve, for example, an outer tube and an inner tube accommodated therein, refer to the aforementioned WO 98/43529 A1. A further option is the so-called three-pipe technique, refer also to the aforementioned U.S. Pat. No. 6,955,644 B2, which describes an endoscope comprising a shaft assembly with three tubes arranged one inside the other.

This arrangement enables a secure sealing of the optical arrangement and other components of the endoscope. However, it has been observed that the assembly of such shaft assemblies involves plenty of effort. This applies to the joining technology necessary for fixing the individual elements, for instance. Established joining techniques for observation instruments include, for example, positive-locking connections, firmly bonded connections, force-locking connections, friction-locking connections, etc.

Firmly bonded connections may include welding, soldering and bonding, for instance. Force-fit and/or friction-fit connections include screw connections, for example. Positive-fit connections include, for example, securing elements such as retaining rings, snap locks and the like. It involves certain challenges to position and join the shafts or tubes involved safely and, if necessary, the components arranged therein with the required accuracy, both at the distal end and at the proximal end of the shaft assembly.

It has also been observed that observation instruments are susceptible to vibrations. Such mechanical stresses can damage the instrument. Similarly, sterilization processes, cleaning processes and similar component loads may also result in damages.

SUMMARY

In view of this, it is an object of the present disclosure to present an observation instrument, wherein the optical arrangement can be easily mounted and is accommodated in the instrument shaft with high positioning accuracy.

It is a further object of the present disclosure to present an observation instrument that is robust and insensitive.

It is a further object of the present disclosure to present an observation instrument that is easy to clean and sterilize.

It is a further object of the present disclosure to present an observation instrument having an optical arrangement that is able to endure mechanical loads and shocks without adversely affecting the function and mechanical integrity of the observation instrument.

It is a further object of the present disclosure to present an assembly concept for the optical arrangement of an observation instrument, which allows the instrument shaft to be arranged with a diameter as small as possible.

It is a further object of the present disclosure to present an observation instrument that is easy to assemble, and that can be assembled repetitively and accurately.

It is a further object of the present disclosure to present improvements in regard of at least one of the drawbacks mentioned above.

It is a further object of the present disclosure to present an observation instrument that is arranged for an accurate positioning of the optical arrangement therein. In some embodiments, this should apply with regard to an arrangement of an objective lens assembly of the optical arrangement with respect to a distal end of the instrument shaft.

It is a further object of the present disclosure to provide for a reliable and durable arrangement and coupling of the optical components.

In accordance with a first aspect, these and other objects are achieved by an observation instrument, in particular an endoscope, comprising a longitudinally extending instrument shaft having a distal end and a proximal end, and an optical arrangement which extends at least sectionally through the instrument shaft, wherein the optical arrangement comprises at least one optical component which is accommodated in a support shaft, and wherein the support shaft is at least axially slidably accommodated in the instrument shaft, at least partially, and is distally preloaded.

In accordance with a further aspect of the present disclosure, these and other objects are achieved by an observation instrument, comprising a longitudinally extending instrument shaft having a distal end and a proximal end, a support shaft arranged in the instrument shaft, and an optical arrangement at least partially disposed in the instrument shaft, wherein the optical arrangement comprises at least one optical component that is arranged in the support shaft, wherein the support shaft is axially slidably supported in the instrument shaft, and wherein the support shaft is distally preloaded in the instrument shaft.

In accordance with a further aspect of the present disclosure, these and other objects are achieved by an endoscope, comprising an instrument shaft having a distal end and a proximal end, a support shaft arranged in the instrument shaft, and an optical arrangement at least sectionally arranged in the instrument shaft, wherein the optical arrangement comprises at least one optical component that is arranged in the support shaft, wherein the support shaft is axially slidably supported in the instrument shaft, wherein the support shaft is distally preloaded in the instrument shaft, and wherein the optical arrangement in the support shaft is at least sectionally preloaded distally relative to the support shaft.

In accordance with a further aspect of the present disclosure, these and other objects are achieved by an endoscopic observation instrument, comprising an instrument shaft having a distal end and a proximal end, a support shaft arranged in the instrument shaft, an intermediate shaft that is arranged between the instrument shaft and the support shaft, and an optical arrangement at least sectionally arranged in the support shaft and thus in the intermediate shaft and the instrument shaft, wherein the optical arrangement comprises at least one optical component that is arranged in the support shaft, wherein the support shaft is axially slidably supported in the instrument shaft, wherein the support shaft is distally preloaded in the intermediate shaft and thus in the instrument shaft, wherein the optical arrangement in the support shaft is at least sectionally preloaded distally relative to the support shaft, and wherein the intermediate shaft closes the support shaft and the optical arrangement arranged therein to the outside.

In accordance with exemplary aspects, the support shaft is arranged in a fashion force-fitted under preloading in the instrument shaft, wherein a force component pre-stresses the support shaft distally. In this way, the support shaft and the optical arrangement at least partially arranged therein are kept in the instrument shaft in a force-fitted manner. This may have the effect that in certain embodiments a distal end of the support shaft can be positioned highly accurate with respect to the distal end of the instrument shaft. The support shaft is arranged in the instrument shaft in a force-fitted manner. The force-fitted support under preloading allows, at least partially, elastic, flexible and error-compensating arrangements or mounting of optical components of the optical arrangement. In this way, a compensation of temperature fluctuations and associated expansions may be possible. In addition, a certain robustness to shocks and other mechanical loads may also result therefrom. Susceptibility to vibrations, oscillations and similar influencing factors are also significantly reduced. Overall, in this way, assembly simplification may also be achieved when the support shaft is preloaded from its proximal end towards the distal end of the instrument shaft. In other words, at the distal end of the support shaft, it is not absolutely necessary to provide fasteners that require intervention during assembly.

In certain embodiments, the support shaft is preloaded on one side. This may include a force-fitted mounting, i.e. positioning under preloading. Accordingly, the support shaft is not fixed at its two ends (distal end and proximal end). Instead, the preloading at the distal end results in an exact positioning. The resulting positioning (relative to the instrument shaft and/or housing of the observation instrument) at the proximal end is performed under prestressing and may therefore include compensation movements. The proximal positioning is therefore not fixed, but variable, at least within limits. Overall, the support shaft can be moved axially relative to the housing, at least within narrow borders defined by the elasticity of the preloading (i. e. of a spring, for instance). The support shaft is disposed in the instrument shaft at least slightly movable in the axial direction.

In certain embodiments, the spring-loaded, slightly movable mounting of at least some optical components may be achieved, for instance, when these optical components—in addition to the arrangement of the support shaft in the instrument shaft under preloading—are accommodated in the support shaft under preloading. In other words, the carrier may serve as a shell or sheath for at least some of the optical components. At least some of the optical components may be pretensioned to the distal end by means of a pretensioning element that is directly or indirectly supported at the support shaft. In addition, however, the support shaft itself may be pretensioned with respect to the instrument shaft to the distal end by means of a pretensioning element that is supported at the housing. The instrument shaft itself is generally fixed to the housing, i.e. sufficiently firmly connected to a head or housing of the observation instrument.

In certain embodiments in accordance with the present disclosure, the support shaft is not only arranged as a short carrier sleeve, but as a shaft having a considerable longitudinal extension between a proximal end and a distal end of the shaft assembly. In certain embodiments, the longitudinal extension of the carrier shaft is almost equal to or even greater than the longitudinal extension of the (outer) instrument shaft. In other words, in accordance with specific embodiments, the support shaft extends into the head piece and/or the housing at the proximal end of the endoscope. Hence, in some embodiments, a length-to-diameter ratio of the shaft is at least 2:1. In further embodiments, the length-to-diameter ratio of the shaft is at least 5:1. In further embodiments, the length-to-diameter ratio of the shaft is at least 10:1.

In accordance with a further exemplary embodiment of the observation instrument, the support shaft is preloaded axially in the instrument shaft against a distal end element that is fixedly attached to the instrument shaft. This support can be provided directly or mediately. For example, the support shaft may directly or mediately contact the distal end element, with the integration of a spacer, as the case may be. The distal end element can be joined directly or indirectly to the support.

In accordance with an exemplary embodiment, the observation instrument further comprises a spacer that is located between the support shaft and a distal end element of the observation instrument that is coupled to the instrument shaft. This simplifies the precise positioning of an objective lens assembly with respect to the distal end of the observation instrument. Thus, the overall imaging quality can be improved.

By way of example, the distal end element may be arranged as a window or pane. The distal end element is generally directly or mediately coupled to the distal end of the instrument shaft. In this way, the distal end element may eventually provide a stop for the support shaft that is supported via the spacer at the end element.

The spacer can be used to easily and highly accurately adjust the distance between a most distally arranged component, which is arranged directly or mediately at the support shaft, and the end element. This design does not exclude that the end element itself is an optically operative component.

Furthermore, the above embodiment involves both observation instruments with a straight direction of view as well as observation instruments with a lateral direction of view that are inclined with respect to a longitudinal axis of the instrument shaft.

According to another exemplary embodiment of the observation instrument, the spacer defines a distance between an objective lens assembly of the optical arrangement and the distal end element. In other words, the support shaft pushes the optical lens assembly against the spacer and thus, while maintaining a defined distance, against the distal end of the instrument shaft. According to an exemplary embodiment, the lens assembly is at least partially accommodated in a support sleeve of the optical lens assembly, which is contacted by the support shaft. Generally, it is also conceivable that the lens assembly may be mounted directly in the support, at least partially. Generally, the optical lens assembly may be glued to the support sleeve or the support shaft.

According to another exemplary design of the observation instrument, the support shaft extends from the distal end of the instrument shaft to the proximal end of the instrument shaft and, in certain embodiments, into a housing of a head piece of the observation instrument. Accordingly, the support shaft is not just a relatively short sleeve.

According to another exemplary embodiment of the observation instrument, the support shaft is preloaded distally by a proximately arranged biasing element that acts on the support shaft. The biasing element is in certain embodiments located at or adjacent to the proximal end of the support shaft.

According to another exemplary embodiment of the observation instrument, the biasing element is arranged between a proximal pressure surface and a distal driving surface that is coupled to the support shaft. The biasing element is supported at its proximal end on the pressure surface. At its distal end, the biasing element acts on the driving surface which is arranged at the support shaft and/or connected to the support shaft. The biasing element urges the proximal pressure surface and the distal driving surface apart from one another. The driving surface is formed, for example, on a mounting sleeve which is coupled to the support shaft.

According to another exemplary embodiment of the observation instrument, the biasing element surrounds an observation beam path of the observation instrument. In other words, the observation beam path or observation path extends through the biasing element. This may involve a concentric alignment between the biasing element and the support shaft. In other words, at least one optical component may extend through the biasing element, at least sectionally, wherein the biasing element and the component are axially aligned with one another.

According to another exemplary embodiment of the observation instrument, the biasing element is arranged as a compression spring. In certain embodiments, the biasing element can be arranged as a coil spring. It goes without saying that fluidic biasing elements, i.e. gas springs or the like, are also conceivable. Furthermore, the biasing element may be basically formed of metal, but alternatively also of plastic materials.

According to another exemplary embodiment of the observation instrument, the optical arrangement in the support shaft is at least sectionally preloaded distally relative to the support shaft. In this way, a spring-loaded, force-fitted secured arrangement of the optical arrangement may result therefrom. A certain capacity for compensating movement in response to loads, pressure or temperature fluctuations is provided. This ensures a high degree of robustness. In other words, the support shaft itself can be preloaded distally, resulting in an abutment at a distal end of the instrument shaft and/or the observation instrument. Furthermore, at least some optical components in the support shaft may be biased distally, wherein a limit stop for the optical components biased distally is provided in the support shaft itself— or coupled thereto. The limit stop in or at the support shaft may be provided by the objective lens assembly, which is accommodated at the distal end of the support shaft according to at least some exemplary embodiments. This may include a firmly bonded mounting of the lens assembly on the support shaft, for example by gluing, soldering or welding.

According to another exemplary embodiment of the observation instrument, the optical arrangement is at least partially axially displaceable in the support shaft, wherein the optical arrangement is at least partially preloaded distally by a further, inner biasing element.

In this way, the observation instrument may include an outer biasing element coupled to the support shaft for distal preloading. Furthermore, the optical arrangement may include an inner biasing element coupled to optical components arranged in the support shaft for distal preloading. The biasing elements may be arranged concentrically to each other.

According to another exemplary embodiment of the observation instrument, the inner biasing element is coupled to at least one optical component, for instance a rod lens, which is arranged in the support shaft. The inner biasing element prestress the at least one optical component distally relative to the support shaft. Accordingly, the optical arrangement may include a rod lens arrangement or rod lens assembly that is proximally adjoining the (distally arranged) lens assembly. The rod lens arrangement may be arranged as Hopkins lens arrangement. The rod lens arrangement comprises several rod lenses, which may be spaced apart by additional components (such as corrective lenses) and/or spacers (distance spacers, spacing rings). In certain embodiments, the rod lens assembly is entirely or nearly entirely arranged in the support shaft. The inner biasing element may preload the rod lens assembly towards a distal limit stop, for instance towards the objective lens assembly. Overall, this hence results in an optical arrangement in the support shaft, which is robust against shocks, vibrations and other mechanical loads.

According to another exemplary embodiment of the observation instrument, the optical arrangement further includes an ocular assembly arranged proximal of the support shaft. In certain embodiments, the inner biasing element is supported at its proximal end directly or mediately at the ocular assembly. Hence, the inner biasing element may be disposed between the ocular assembly and the rod lens assembly.

This may include embodiments, wherein the inner biasing element preloads the ocular assembly proximally and the rod lens assembly distally. In this way, the ocular assembly may be flexibly mounted in the axial direction, for instance with regard to the axial positioning of the ocular assembly with respect to a housing and/or a distal end of the instrument shaft. This may include a "floating" positioning of the ocular assembly.

An exemplary embodiment includes a fixed/rigid coupling of the ocular assembly with the support shaft. Thus, the ocular assembly (e.g. via a support tube) is preloaded distally together with the support shaft by the outer biasing element. This may involve axial relative movements, for instance axial compensating movements, relative to the support shaft. This may involve embodiments, wherein the axial position of the ocular assembly with respect to the support shaft is adjustable, for example by means of adjustment during assembly of the observation instrument.

Another exemplary embodiment includes a fixed/rigid coupling of the ocular assembly with the instrument shaft and or the housing of the observation instrument. Thus, the support shaft is preloaded distally by the outer biasing element relative to the instrument shaft and relative to the ocular assembly. This may include embodiments, wherein the axial position of the ocular assembly is adjustable with respect to the instrument shaft and/or the housing, for example by means of adjustment during assembly of the observation instrument.

Furthermore, according to a further exemplary embodiment of the observation instrument, a rotary position locking element is provided which defines a rotational position of the support shaft, which is accommodated under preloading, with respect to the instrument shaft and/or the housing of the observation instrument.

According to further exemplary embodiments, the ocular assembly is at least sectionally accommodated in a housing and/or head of the observation instrument. Accordingly, the ocular assembly is not or not substantially accommodated in the support shaft and/or the instrument shaft. When the ocular assembly is mounted in the housing, the ocular assembly may basically have a diameter larger than a possible diameter provided by the support shaft. By way of example, the housing of the observation instrument may define an axial relative position of the ocular assembly. Furthermore, the housing of the observation instrument can directly or mediately provide a proximal limit stop for the ocular assembly.

According to another exemplary embodiment of the observation instrument, an intermediate shaft is arranged between the instrument shaft and the support shaft, which surrounds the support shaft. In this way, a three-pipe arrangement of the shaft assembly of the observation instrument may be provided.

In this embodiment, the instrument shaft forms an outer shaft of the observation instrument, which provides a certain mechanical stability. The intermediate shaft may also be referred to as inner shaft, cf. U.S. Pat. No. 6,955,644 B2. Generally, an intermediate space is formed between the instrument shaft and the intermediate shaft, which is used, for example, to accommodate optical fibers. Basically, the instrument shaft and the intermediate shaft may be arranged concentrically to each other. However, embodiments are conceivable, wherein the instrument shaft and the intermediate shaft are arranged parallel to each other, wherein, however, the longitudinal axes of the instrument shaft and the intermediate shaft are spaced apart from one another.

The intermediate shaft may provide a hermetic seal of the optical arrangement. The intermediate shaft is used to accommodate the support shaft and the optical components mounted in or on it. Accordingly, the support shaft may serve as a guide for at least parts of the optical arrangement. The support shaft allows a highly accurate concentric arrangement of the optical components. The support shaft and the intermediate shaft may be concentrically aligned to each other.

According to exemplary embodiments, the distal end element is arranged on or in the intermediate shaft. At the distal end of the observation instrument, the instrument shaft and the intermediate shaft can be coupled to one another, for example by a firmly bonded connection. According to this embodiment, the intermediate shaft is fixedly attached in the instrument shaft. The support shaft is preloaded by the biasing element towards the distal end of the intermediate shaft and/or the instrument shaft and positioned with high accuracy.

According to a further exemplary embodiment of the observation instrument, the intermediate shaft is at the distal end fixedly attached to the instrument shaft. The intermediate shaft is glued to the instrument shaft, for example. It is also conceivable to arrange a ring-shaped coupling element between the instrument shaft and the intermediate shaft. Furthermore, embodiments are conceivable, wherein the distal end element is fixedly attached to both the instrument shaft and the intermediate shaft. The embodiments described above involve that no axial relative movement is desired between the instrument shaft and the intermediate shaft, at least at the distal end.

According to another exemplary embodiment of the observation instrument, the intermediate shaft closes the support shaft and the optical arrangement contained therein to the outside. In other words, the intermediate shaft is used as a cover and/or seal for the optical arrangement. This applies in accordance with certain embodiments to a radial and a distal sealing. A proximal sealing can be achieved through the housing.

It is to be understood that the previously mentioned features and the features mentioned in the following may not only be used in a certain combination, but also in other combinations or as isolated features without leaving the spirit and scope of the present disclosure.

BRIEF DESCRIPTION OF THE DRAWINGS

Further features and advantages of the disclosure are disclosed by the following description of a plurality of exemplary embodiments, with reference to the drawings, wherein.

DETAILED DESCRIPTION OF EXEMPLARY EMBODIMENTS

Figure 1:
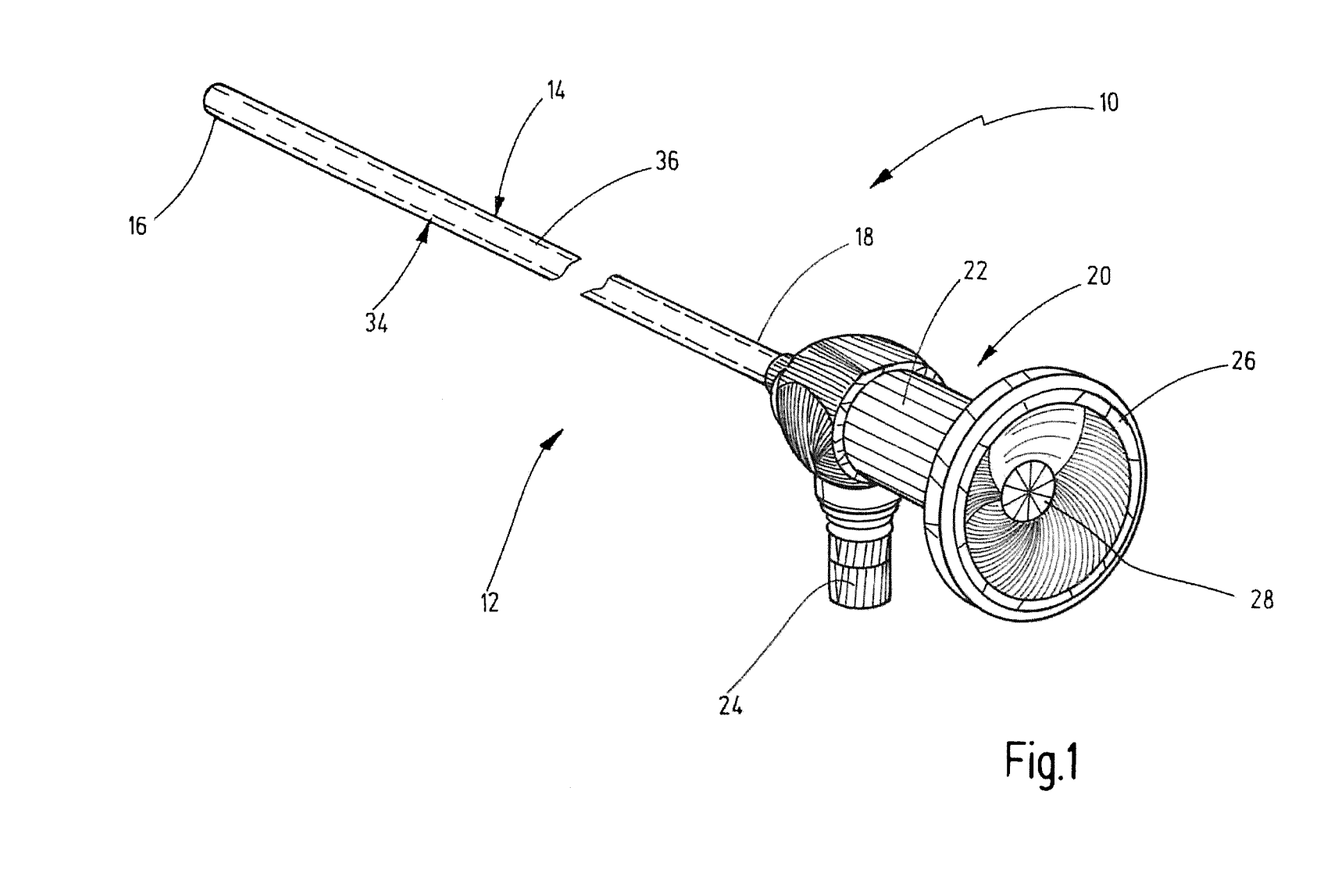
FIG. 1 is a perspective rear view of an observation instrument that is arranged as an endoscope, comprising a broken view of an instrument shaft.

FIG. 1 shows a perspective rear view of an exemplary embodiment of an observation instrument 10 that is arranged as an endoscope 12. Fields of application for the observation instrument 10 may involve medical purposes, but also technical purposes.

The instrument 10 comprises an instrument shaft 14, which is shown in FIG. 1 in a broken view. The instrument shaft 14 has a considerable length-to-diameter ratio. During use for medical purposes, the instrument shaft 14 may be inserted into body openings to allow observations.

The instrument shaft 14 comprises a distal end 16 and a proximal end 18. The distal end 16 of the instrument shaft 14 defines a distal end of the instrument 10, and a head piece 20, also referred to as a housing 22, is adjoining the proximal end 18 of the instrument shaft 14. By way of example, an illumination connection 24 is also provided at the housing 22, via which light guides or the like may be coupled. An eyepiece cup 26, which surrounds an eyepiece window 28, is also arranged at the housing 22. The eyepiece cup 26 is arranged at a proximal end of the housing 22 that is opposite a distal end of the housing 22, from which the instrument shaft 14 extends towards the distal end 16 of instrument 10. It goes without saying that the instrument 10 may also have an image sensor, as an alternative or in addition to the eyepiece cup 26 that is provided with the eyepiece window 28. Such an instrument 10 may also be referred to as an eyepieceless instrument. However, this does not exclude that the instrument 10 is equipped with a so-called ocular assembly.

The instrument 10 comprises an optical arrangement 34, which is indicated by a dashed line in FIG. 1. The optical arrangement 34 extends at least sectionally through the instrument shaft 14. In certain embodiments, the optical arrangement 34 extends from a distal end 16 of the instrument shaft 14 into the housing 22. Depending on the perspective, the eyepiece window 28 may also form part of the optical arrangement 34. The optical arrangement 34 comprises a plurality of optical components. This may involve, for instance, an objective lens assembly disposed at the distal end 16 of the instrument shaft 14. Furthermore, the optical arrangement 34 may involve an ocular assembly which is accommodated, for example, in the housing 22. A rod lens assembly may be disposed between the objective lens assembly and the ocular assembly, which may also arranged as a Hopkins lens assembly. The optical arrangement 34 defines an observation beam path 36 through the instrument 10.

Instrument 10 may comprise a plurality of shafts or tubes arranged between the distal end 16 and the proximal end 18. For illustrative purposes, reference is made in this context to the simplified illustration in FIG. 2. In particular with regard to wall thicknesses and other proportions, the representation in FIG. 2 is, for illustrative reasons, exaggerating and/or not true to scale.

Figure 2:
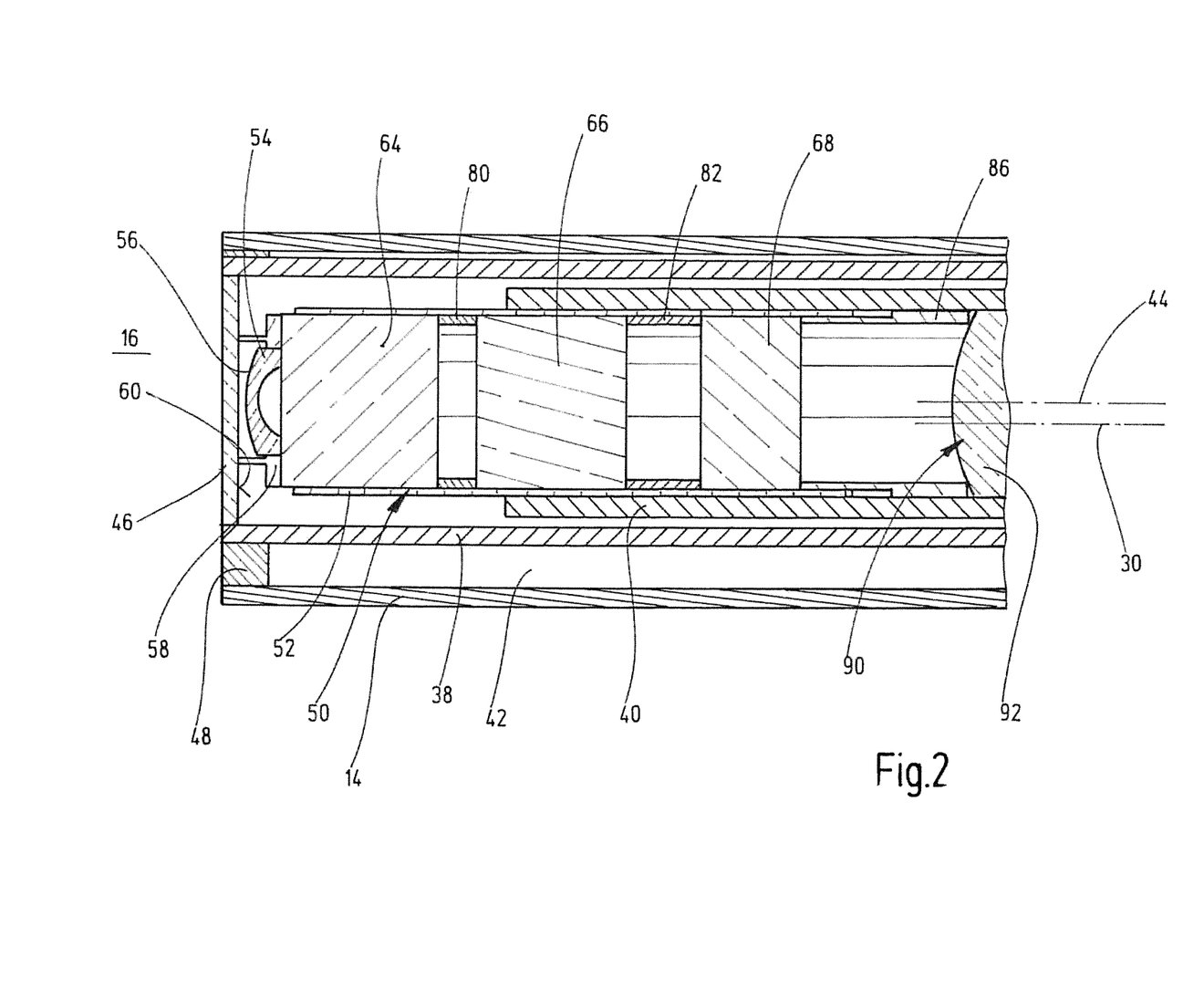
FIG. 2 is a schematic, simplified sectional view of a distal region of an instrument shaft.

FIG. 2 shows a distal portion of the instrument shaft 14 disposed at the distal end 16. A central longitudinal axis of the instrument shaft 14 is designated by 30 in FIG. 2. An intermediate shaft 38 is accommodated in the instrument shaft 14. A support shaft 40 is accommodated in the intermediate shaft 38. Overall, the support shaft 40, the intermediate shaft 38 and the instrument shaft 14 together form an arrangement having three tubes or shafts which are arranged one inside the other. An intermediate space between the intermediate shaft 38 and the instrument shaft 14 is designated by 42. By way of example, the intermediate shaft 38 and the support shaft 40 are concentrically aligned to each other and provided with a common longitudinal axis 44. By way of example, the instrument shaft 14 is eccentrically aligned with respect to the intermediate shaft 38 and/or to the support shaft 40. Accordingly, in the exemplary embodiment illustrated, a longitudinal axis 30 of the instrument shaft 14 is spaced away from the (common) longitudinal axis 44 of the intermediate shaft 38 and the support shaft 40. Concentric arrangements of the three shafts 14, 38, 40 are also conceivable. The shafts 14, 38, 40 are generally cylindrical and provided with circular and/or annular cross-sections. However, deviating, non-circular arrangements are also conceivable.

At the distal end 16, an end element 46 is provided. By way of example, the distal end element 46 is arranged on the intermediate shaft 38. Furthermore, a closure cap 48 is indicated between the instrument shaft 14 and the intermediate shaft 38. However, it is also conceivable to couple the end element 46 both with the intermediate shaft 38 and directly with the instrument shaft 14. Generally, the instrument shaft 14 is fixedly attached to the intermediate shaft 38 at the distal end 16. This may be achieved, for example, by means of a firmly bonded connection, e.g. by gluing, soldering or welding. However, it is also conceivable to provide an adapter between instrument shaft 14 and intermediate shaft 38 to form the closure. Furthermore, light guides received in the intermediate space 42 may occupy a part of a distal end surface of the intermediate space 42. The light guides or light fibers can be retained by cementing. As already indicated above, the end element 46 may also provide the coupling between the instrument shaft 14 and the intermediate shaft 38.

The intermediate shaft 38 provides a guide for the support shaft 40. A lens assembly 50 is accommodated in the intermediate shaft 38. The support shaft 40 is used as a carrier for the lens assembly 50. By way of example, the lens assembly 50 is arranged in a sleeve 52 which is connected to the support shaft 40. It goes without saying that lens assembly 50 may also be mounted directly in the support shaft 40. The implementation of the sleeve 52 can be utilized to at least partially preassemble the lens assembly 50. By way of example, the sleeve 52 is connected to the support shaft 40 in a firmly bonded manner, e.g. by gluing, soldering or welding.

The objective lens assembly 50 comprises several optical components. By way of example, the objective lens assembly 50 comprises a distally arranged component 54, which is arranged as an aspherical lens 56. FIG. 2 also shows that the objective lens assembly 50 is supported on the distal end element 46, i.e. on a distal limit stop of the instrument 10, via a spacer 58. In this way, for instance, a distance between the end element 46 and the component 54 can be adjusted with high precision. The distal end element 46 provides an abutment surface 60 on which the spacer 58 is supported. The end element 46 may be also crescent-shaped or similarly shaped, and therefore does not necessarily have to be ring-shaped and closed.

In addition to the component 54, the lens assembly 50 comprises, for example, further components 64, 66, 68, which may be arranged as lenses, prisms, lens packages and/or prism packages respectively. Further, spacers 80, 82 may be provided, which are ring-shaped. Overall, the objective lens assembly 50 may form a compact unit, especially when using a sleeve 52. The support shaft 40, which is in certain embodiments fixedly attached to the objective lens assembly 50, for instance to the sleeve 52, is preloaded towards the distal end 16. It is ensured in this way that the component 54 and, as the case may be, other adjacent components come to an abutment with the end element 46 in a defined manner.

In FIG. 2, there is further indicated a pressure piece 86 that is arranged between objective lens assembly 50 and a rod lens assembly 90. Both the rod lens assembly 90 and the objective lens assembly 50 are associated with the optical arrangement 34, which may also include an ocular assembly. The rod lens assembly 90 may be pressed against the objective lens assembly 50 via the thrust piece 86, for example against a proximal component 76 of the objective lens assembly 50. The rod lens assembly 90 comprises a rod lens 92, which may also be referred to as an optical component of the rod lens assembly 90.

In the exemplary embodiment shown in FIG. 2, by way of example, the component 64 is glued or otherwise joined to the sleeve 52. The sleeve 52 is glued or otherwise joined to the support shaft 40. The component 64 contacts the spacer 58. The component 54 is coupled to the component 64 and/or the spacer 58. A biasing force may be applied to the sleeve 52 via the support shaft 40, and to the component 64 via the sleeve 52. Hence, this allows the component 64 to press against the spacer 58 and to bring it into contact with the abutment surface 60 of the end element 46.

Another preloading may result from a distally directed force that also acts on the rod lens assembly 90. The force can act on the push piece 86 via the rod lens 92, and via the push piece 86 on the elements 68, 82, 66, 80, 64 of lens assembly 50, in order to preload the same towards the component 64. In this way, both the support shaft 40 and the optical arrangement 34 arranged therein or thereon are preloaded distally. The spacer 58 defines an axial position and/or axial limit stop for the components of the optical arrangement 34.

Figure 3:
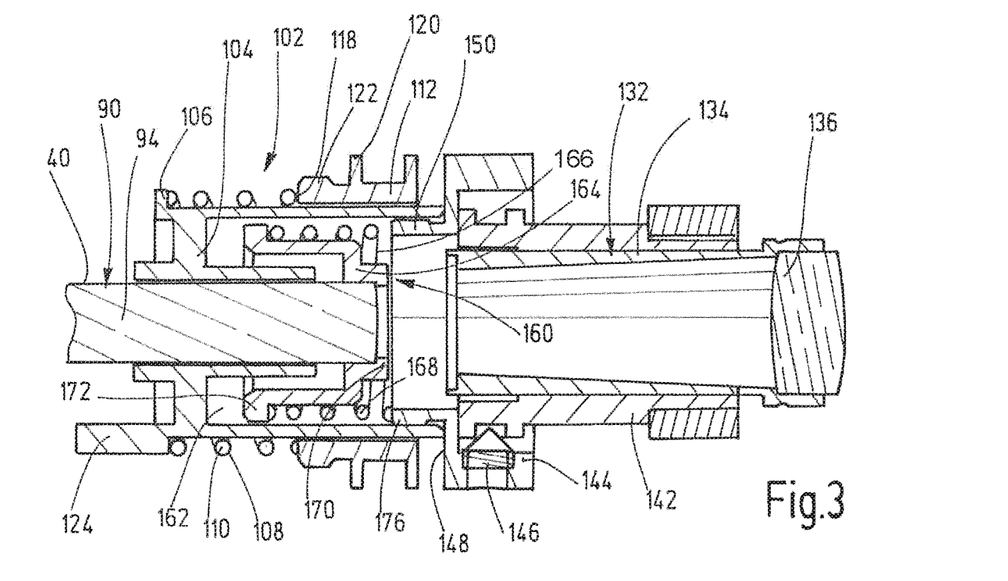
FIG. 3 is a sectional view of a proximal region of a support shaft in which a rod lens assembly is arranged, wherein an ocular assembly adjoins the rod lens assembly.
Figure 4:
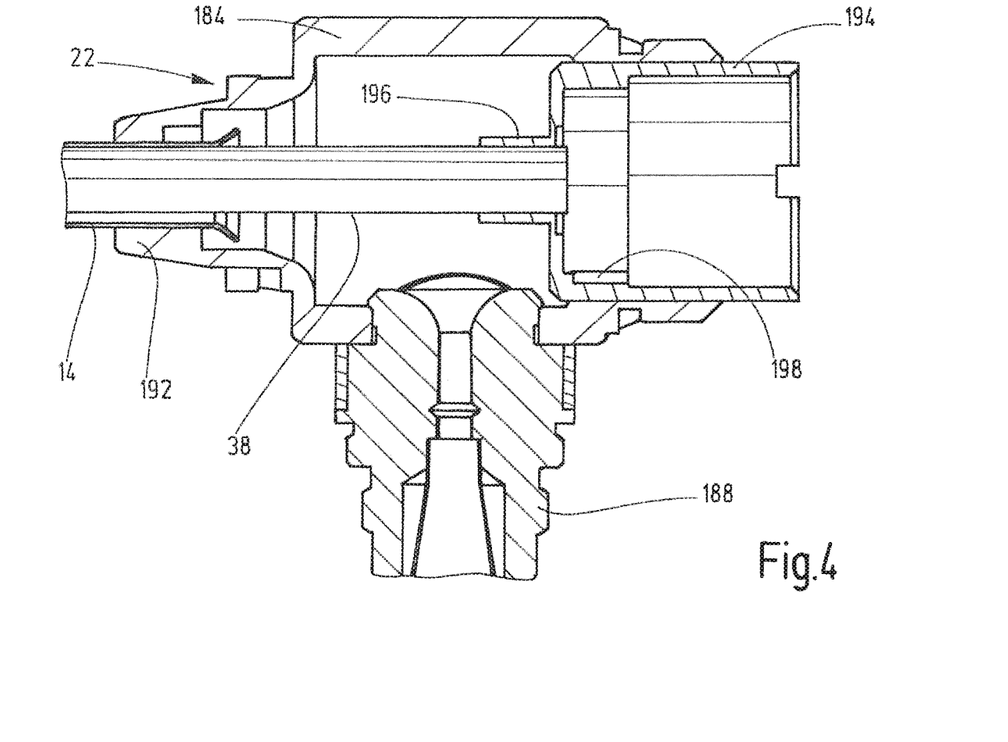
FIG. 4 is a sectional view of a housing or head piece of an observation instrument that is arranged as an endoscope, in which an instrument shaft and an intermediate shaft are arranged.
Figure 5:
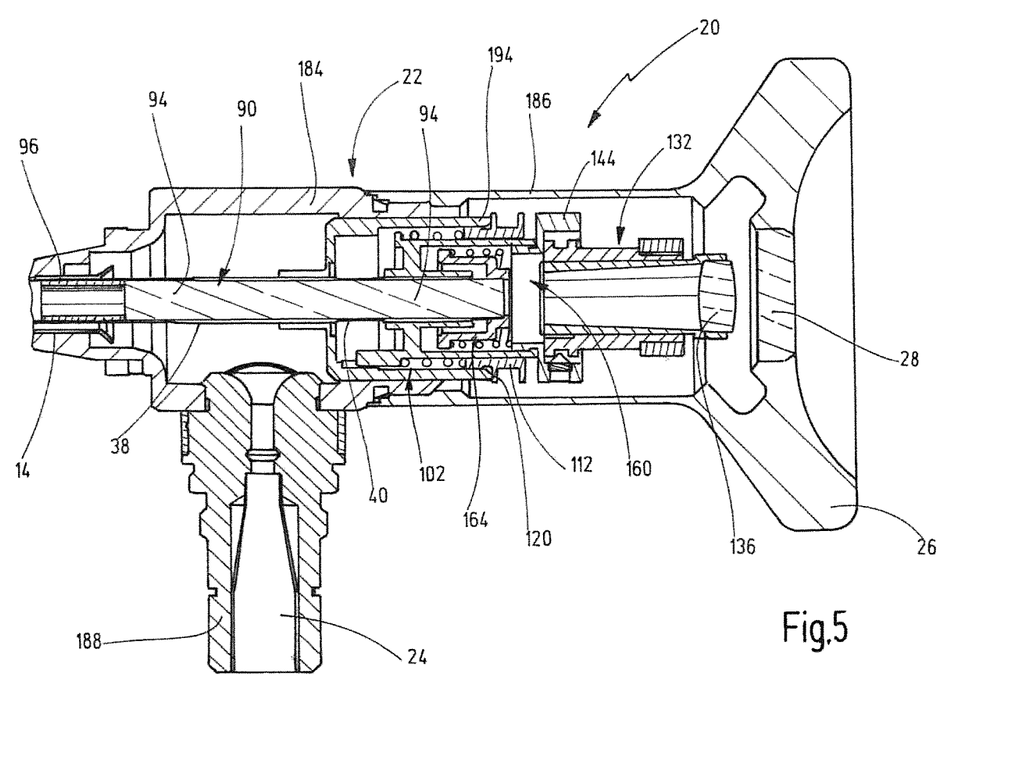
FIG. 5 is a sectional view of a proximal portion of an observation instrument comprising the arrangement according to FIG. 3 and the arrangement according to FIG. 4, in an assembled state.

In addition to the Illustration of the distal portion of FIG. 2, FIGS. 3, 4 and 5 illustrate a proximal portion of an instrument 10 that is arranged as an endoscope 12. FIG. 3 elucidates components that may be accommodated in a housing arrangement as shown in FIG. 4. FIG. 5 shows an assembled state of the proximal end of the instrument 10. As opposed to the exaggerated illustration of FIG. 2, FIGS. 3, 4 and 5 show that the shafts 14, 38 and 40 each have only a small wall thickness.

FIG. 3 elucidates a proximal end of the support shaft 40 in which the rod lens assembly 90 is accommodated. In FIG. 3 a proximal rod lens indicated by 94 is partially shown. Additional rod lenses, other optical components, spacers and the like may be accommodated in the support shaft 40 between the rod lens designated by 92 in FIG. 2 and the rod lens designated by 94 in FIG. 3. Generally, these components, for instance also the rod lenses 92, 94, are accommodated in the support shaft 40 in an axially displaceable manner.

A preloading unit 102 is coupled to support shaft 40. The preloading unit 102 comprises a mounting sleeve 104, which is fixedly attached to the support shaft 40 at a proximal and thereof. The mounting sleeve 104 comprises a driving surface 106, which may also be referred to as a distal driving surface or a distal driving collar. Further, the preloading unit 102 comprises a biasing element 108, which is arranged as a spring element 110 for instance. The biasing element 108 extends between a retaining piece 112 and the driving surface 106 of the mounting sleeve 104. The retaining piece 112 is arranged at a proximal end of the biasing element 108. The driving surface 106 is arranged at a distal end of the biasing element 108.

A pressure surface 118 for the biasing element 108 is formed at the retaining piece 112. Further, a housing-side limit stop surface 120 is formed, refer also to FIG. 5. Further, the retaining piece 112 comprises a thread 122, by means of which the retaining piece 112 may be coupled to an inner housing 194 (cf. FIG. 4). By way of example, the mounting sleeve 104 comprises a rotary position lock 124 in the form of a lug at the distal end of the mounting sleeve 104.

The biasing element 108 is supported on the pressure surface 118 of the retaining piece 112 and urges the mounting sleeve 104 distally. FIGS. 3, 4 and 5 illustrate in conjunction that the retaining piece 112 in the joined state is fixedly attached to the head piece 20 or housing 22 of instrument 10 via an inner housing 194. Thus, the biasing element 108 urges the support shaft 40 via the mounting sleeve 104 towards the distal end 16 of the instrument 10. Eventually, this causes a sudden pressure of the objective lens assembly 50 against the spacer 58, which rests on distal end element 46.

Optical components, for instance the rod lenses 92, 94 of rod lens assembly 90 and at least some components of the objective lens assembly 50, which are accommodated axially displaceable in support shaft 40, are preloaded distally by another biasing unit 160. This is explained in more detail herein below.

FIG. 3 further shows that an ocular assembly 132 adjoins the rod lens assembly 90. The ocular assembly 132 is arranged at the proximal end of the rod lens assembly 90. The lens assembly 50 (FIG. 2) is arranged at the distal end of the rod lens assembly 90. The ocular assembly 132 comprises, for example, a tube 134 which accommodates at least one optical component 136 that is arranged as a lens, for instance. In the assembled state (see FIG. 5), the component 136 of the ocular assembly 132 is arranged adjacent to the eyepiece window 28 of the eyepiece cup 26 to make the optical image visible to an observer. The ocular assembly 132 may comprise several optical components.

FIG. 3 shows that the ocular assembly 132 is mounted on a sleeve-like carrier 142 via the tube 134. The carrier 142 is connected to a clamping piece 144 and fixed to the clamping piece 144 by at least one clamping element 146. By way of example, the clamping element 146 is a grub screw (headless screw) that extends radially in a groove or recess on the circumference of the carrier 142.

The clamping piece 144 has a limit stop surface 148 which defines an axial relative position of the clamping piece 144 with respect to the mounting sleeve 104. The clamping piece 144 may be connected force-fitted to the mounting sleeve 104 via a thread 150. The limit stop (abutment) surface 148 defines a screw-in depth of the clamping piece 144 at the locating sleeve 104.

The preloading unit 160 is disposed in a recess 162 of the mounting sleeve 104. The recess 162 is cup-shaped or arranged as an annular groove. The preloading unit 160 comprises a connecting piece 164, which is arranged like a sleeve, for instance. The connecting piece 164 is coupled to a proximal component of the rod lens assembly 90, for instance to the rod lens 94. The preloading unit 160 comprises a biasing element 166. The biasing element 166 may also be referred to as inner biasing element. By contrast, the biasing element 108 may also be referred to as outer biasing element. By way of example, the biasing elements 108, 166 are concentrically aligned with respect to one another.

The biasing element 166 is arranged as a spring 168, for instance as a coil spring. The biasing elements 108, 166 are arranged as compression springs, by way example. The biasing element 166 extends between connector piece 164 and clamping piece 144. The biasing unit 160 is interposed between the rod lens assembly 90 and the ocular assembly 132.

The biasing element 166 rests distally on a (limit) stop surface 172 of the connector piece 164. The connector piece 164 comprises a driving collar 170 that at a proximal end engages the rod lens 94 and pushes the same distally. At its proximal end, the biasing element 166 rests on a contact surface 176 that is formed at the clamping piece 144. The preloading unit 160 provides axial preloading between components of objective lens assembly 50, rod lens assembly 90, and ocular assembly 132. In this way, the optical components can be accommodated with nearly no backlash (axially seen). Furthermore, any changes in length, shocks, vibrations and other mechanical loads may be at least partially compensated for, without causing internal stresses that may cause damages at components. At the distal end of the support shaft 40 (FIG. 2), for example, the component 64 is (via the sleeve 52) fixedly attached to the support shaft 40. This provides a distal limit stop for the pre-stressed components.

The preloading unit 102 urges the support shaft 40 towards the distal end 16 of the instrument 10. In this way, high-precision distal axial alignment and positioning of the optical arrangement 34 is enabled, as the contact with the spacer 58 provides a distal axial position reference and/or a limit stop.

FIG. 4 elucidates with reference to a sectional view a configuration of a housing 22 of an instrument 10 that is configured for accommodating the arrangement illustrated in FIG. 3. By way of example, the housing 22 comprises a distal housing section 184 followed by a proximal housing section 186 (only shown in FIG. 5). FIG. 5 fertile shows that the housing section 186 can be used, for example, to accommodate the eyepiece cup 26 and the eyepiece window 28. Furthermore, housing 22 comprises a housing section 188 that accommodates the illumination connection 24.

A guide flange 192 is formed at the housing section 184. The guide flange 192 defines a distal end of the housing 22. The instrument shaft 14 is mounted at the guide flange 192. By way of example, this involves a fixed coupling of the instrument shaft 14 to the guide flange 192. This may include a force-fit, firmly bonded and/or positive-fit coupling, for instance.

The intermediate shaft 38 is accommodated in the instrument shaft 14. The intermediate shaft 38 and the instrument shaft 14 are arranged parallel and offset to one another (i.e. not concentric). The intermediate shaft 38 protrudes from the proximal end of the instrument shaft 14.

An inner housing 194 is also provided at the housing 22, for instance at the housing section 184. The inner housing 194 is fixedly attached to the housing 22. An intermediate flange 196 is formed on the inner housing 194. A proximal end of the inner housing 194 is coupled to the intermediate flange 196. The inner housing 194 seals the intermediate shaft 38 via its intermediate flange 196. Further, a rotary position lock 198 is formed on the inner housing 194, which interacts with the rotary position lock 124 of the mounting sleeve 104. The rotary position lock 124 is exemplarily arranged as a lug. By way of example, the rotary position lock 198 is arranged as a groove or recess which can be engaged by the lug. In this way, the inner housing 194 defines a rotational position of the mounting sleeve 104 relative to the housing 22.

FIG. 5 illustrates the spring-loaded, at least partially "floating" mounting of the optical arrangement 34. A housing-side reference for the preloading unit 102 results from the abutment of the retaining piece 112 on the inner housing 194 that is fixed to the housing. Thus, the biasing element 108 is supported mediately on the housing 22 and presses the mounting sleeve 104 and the components received thereon/therein towards the distal end 16 of the instrument 10. The mounting sleeve 104 is coupled to the retaining piece 112 and thus to the housing 22 in an axially displaceable manner. The clamping piece 144, which defines a position reference for the ocular assembly 132 and thus also for the preloading unit 160, is arranged at the mounting sleeve 104.

The biasing element 166 of the preloading unit 160 is supported by the clamping piece 144 and presses the rod lens assembly 90 distally via the connector 164. This may include an axial relative movement between the rod lens assembly 90 (and, as the case may be, other optical components) and the support shaft 40. As illustrated in FIGS. 3, 4 and 5, ocular assembly 132 is fixedly coupled (i.e. without axial relative movement) to the support shaft 40 via the mounting sleeve 104. Further, FIG. 5 shows that the support shaft 40 protrudes axially beyond the proximal end of the intermediate shaft 38.

Figure 6:
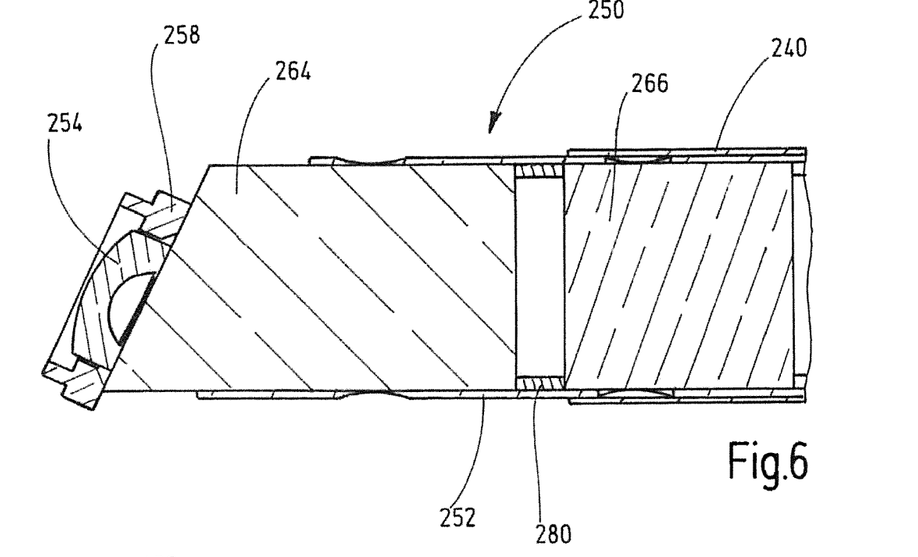
FIG. 6 a sectional view of a distal region of a support shaft comprising an objective lens assembly mounted thereon.
Figure 7:
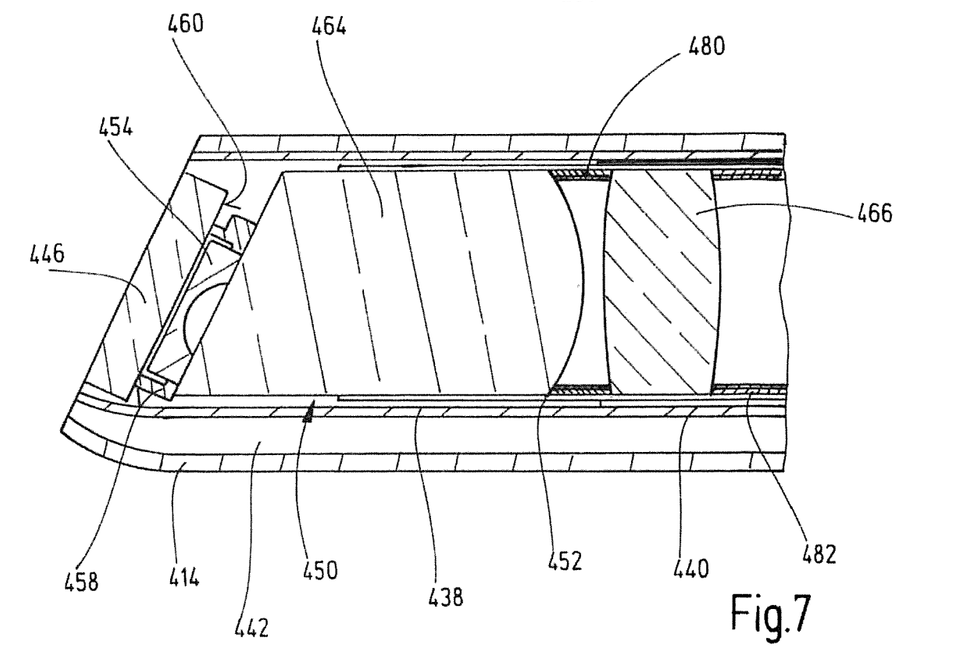
FIG. 7 is a sectional view of a distal region of an instrument shaft in which an objective lens assembly is arranged that is arranged on a support shaft and, via the support shaft, in an intermediate shaft.
Figure 8:
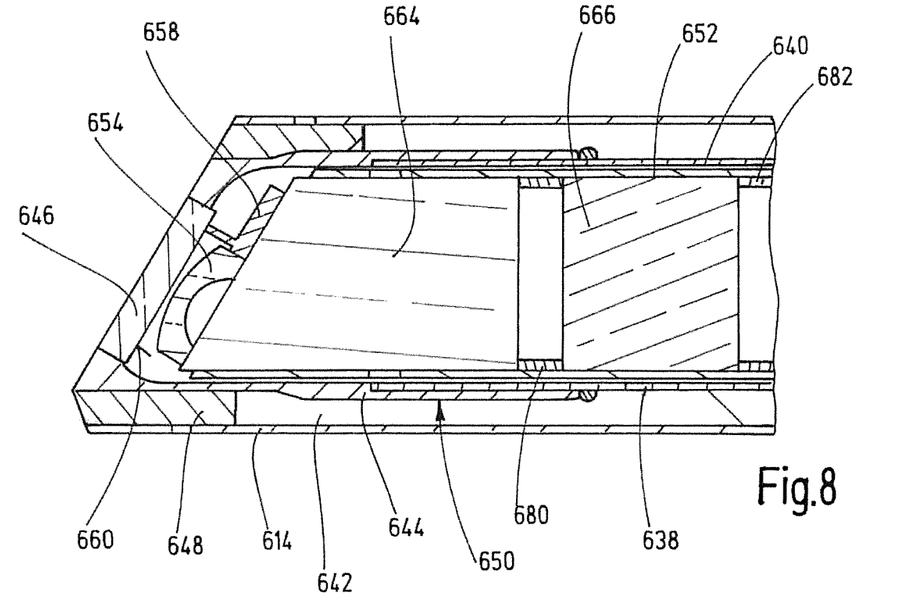
FIG. 8 is a further sectional view of a distal region of an instrument shaft in which an objective lens assembly is disposed that is arranged at a support shaft that is disposed in an intermediate shaft.

FIGS. 6, 7, 8 and 9 illustrate further exemplary embodiments of optical arrangements for observation instruments in which an (inner) support shaft is preloaded distally in a similar manner, wherein further optical components that are arranged in the support shaft are preloaded distally relative to the support shaft. The components illustrated in FIGS. 6, 7 and 8 show observation instruments having a lateral viewing direction, wherein an angular offset to the longitudinal axis of the respective instrument shaft is provided.

FIG. 6 shows a section through a distal section of a support shaft 240. For illustrative purposes, the corresponding representation of the instrument shaft and, where available, the intermediate shaft, is omitted in FIG. 6.

The support shaft 240 carries an objective lens assembly 250 that is mounted arranged at a sleeve 252. As an example, the sleeve 252 is firmly bonded, force-fitted, positive-fitted or otherwise joined with the support shaft 240. The lens assembly 250 includes several optical components, such as a distally arranged component 254. Further, FIG. 6 illustrates a spacer 258 that can be used to preload the lens assembly 250 towards a distal limit stop of the instrument. This may be achieved by axially preloading the support shaft 240, which transmits this preloading via the sleeve 252 to the objective lens assembly 250. Hence, the lens assembly 250 may be pressed against the spacer 258. The spacer 258 may thus ensure a desired nominal position for the component 254.

In addition to the component 254, the lens assembly 250 includes further components or subassemblies 254, 264, 266, and at least one spacer 280, by way of example. At least some of the components may be biased distally relative to the support shaft 240 and/or relative to the sleeve 252 so that an arrangement corresponding to the embodiments shown in FIGS. 2 to 5 is provided.

FIG. 7 shows a sectional view through a distal portion of an instrument shaft 414 in which a support shaft 440 carrying an objective lens assembly 450 is arranged. The configuration of the support shaft 440 and the objective lens assembly 450 according to FIG. 7 basically corresponds to the embodiment already shown in FIG. 6.

The support shaft 440 is accommodated in an intermediate shaft 438, which is arranged in the instrument shaft 414. An intermediate space 442 is defined between the instrument shaft 414 and the intermediate shaft 438. A distal end element 446 is arranged at the distal end of the instrument shaft 414, which is accommodated in the shaft 438, by way of example. The end element 446 may be firmly bonded, positive-fitted, connected via fastening parts or otherwise arranged in the intermediate shaft 438. Further, a fixed connection between the instrument shaft 414 and the intermediate shaft 438 is provided at the distal end, which in turn can be firmly bonded and/or formed by appropriate fastening elements.

The support shaft 440 carries the objective lens assembly 450, which in turn is at least partially accommodated in a sleeve 452. The sleeve 452 is connected to the support shaft 440. The support shaft 440 pushes the sleeve 452 and thus the objective lens assembly 450 towards the end element 446. The objective lens assembly 450 comprises a component 454 that is arranged at the distal end of the objective lens assembly 450. The lens assembly further comprises components or subassemblies 464, 466 and spacers 480, 482.

At least the component 454 or the component 464 is coupled to a spacer 458 to push the same distally towards the end element 446, for instance towards an abutment surface 460 of the end element 446. In this way, a desired distance between the end element 446 and the component 454 may be provided. At least some of the components of the objective lens assembly 450, especially at a distal end of the sleeve 452, are fixedly attached to the sleeve 452, for example by gluing, soldering or a similar appropriate joining process. Hence, the support shaft 440 may apply pressure to the respective component via the sleeve 452 and urge the spacer 458 into contact with the end element 446. The required preloading force can be applied via an outer preloading unit (cf. the preloading unit 102 in FIG. 3).

Generally, at least some of the components of objective lens assembly 450, for instance at the proximal end of the sleeve 452, may be axially displaceable. In this way, a preloading force, which may be applied approximately via an inner preloading unit (refer to the preloading unit 160 in FIG. 3), may be transmitted towards the distal end of the objective lens assembly 450. This may enable the desired axial alignment of the elements of the optical arrangement in the instrument shaft 414. In certain embodiments, the preloading force may be transmitted via the elements of a rod lens assembly, which is not explicitly shown in FIGS. 6 and 7.

FIG. 8 illustrates a further sectional view of a distal section of an instrument shaft 614. An intermediate shaft 638 is accommodated in the instrument shaft 614. A support shaft 640 is accommodated in the intermediate shaft 638. An intermediate space 642 is defined between the instrument shaft 614 and the intermediate shaft 638. The intermediate shaft 638 comprises an end piece 644 at its distal end. A distal end element 646 is arranged at the end piece 644. In FIG. 8 the three shafts 614, 638, 640 are all concentrically aligned to each other.

Between the instrument shaft 614 and the end piece 644 of the intermediate shaft 638 there is arranged a locking ring 648, which surrounds the end piece 644 and the end element 646, for example. In this way, the distal end of the instrument shaft 614 is hermetically sealed, which includes a fixed connection between the intermediate shaft 638 and the instrument shaft. The support shaft 640 carries a lens assembly 650. The lens assembly 650 comprises a 652 sleeve that is coupled to the support shaft 640. Generally, the sleeve 652 may also be integrally formed with the support shaft 640.

The objective lens assembly 650 comprises a component 654 formed at the distal end of the objective lens assembly 650. A distance between the component 654 and the end element 646 is defined by a spacer 658 disposed between the lens assembly 650 and the and element 646, and contacting an abutment surface 660 of the and element 646. Further, the optical lens assembly 650 comprises components or subassemblies 664, 666. In addition, FIG. 8 shows spacers 680, 682 that are ring-shaped, for instance.

Figure 9:
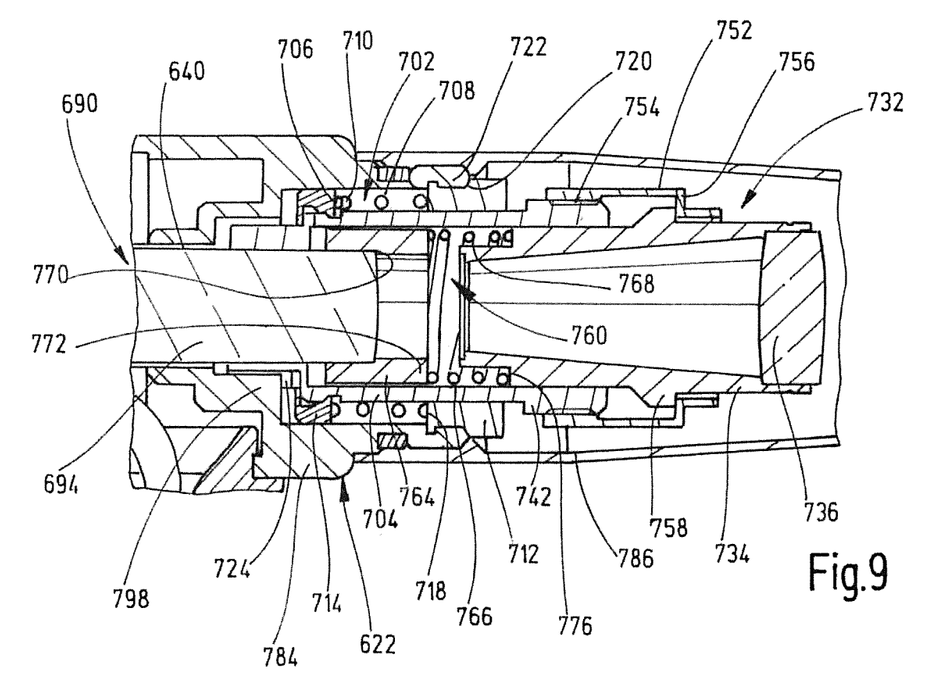
FIG. 9 is a sectional partial view of a head area of an observation instrument in which an ocular assembly is arranged, wherein a rod lens assembly is proximally adjoining the ocular assembly.

FIG. 9 illustrates a sectional view through a proximal portion of a housing 622 of an observation instrument. The distal section shown in FIG. 8 and the proximal section shown in FIG. 9 may be assigned to one and the same embodiment, whereby the representation is not necessarily true to scale. The view in FIG. 8 is enlarged compared to the view in FIG. 9.

The housing 622 shown in FIG. 9 in a partial sectional view is basically similar to the housing 22 shown in FIGS. 4 and 5. The support shaft 640 already partially shown in FIG. 8 extends at least partially into the housing 622 shown in FIG. 9. Another rod lens assembly 90 is arranged on or in the support shaft 640 adjacent to the objective lens assembly 650 shown in FIG. 8 that comprises a rod lens 694, for instance.

The housing 622 comprises housing sections 684, 686, of which the housing section 684 is arranged distally and the housing section 686 is arranged proximally.

FIG. 9 further illustrates an ocular assembly designated by 732 that is at least similar to the ocular assembly 132 shown in FIG. 3. The ocular assembly 732 comprises a tube 734 that carries at least one component 736. In conjunction, FIGS. 8 and 9 show that the rod lens assembly 690 is disposed between the objective lens assembly 650 and the ocular assembly 732.

Similarly, as already elucidated with reference to the FIGS. 3, 4 and 5, the embodiment according to FIGS. 8 and 9 also includes a first preloading unit 702 and a second preloading unit 760. The first preloading unit 702 may also be referred to as outer preloading unit. The second preloading unit 760 may also be referred to as inner preloading unit. The preloading unit 702 is used to generate a distally directed pretensioning force onto the support shaft 640. The preloading unit 760 is used to generate an axial pretensioning force for the axial positioning of elements of the optical arrangement of the observation instrument. Thus, the preloading unit 760 may distally preload components of the rod lens assembly 690 and, as the case may be, also of the objective lens assembly 650.

The preloading unit 702 comprises a mounting sleeve 704 that is fixedly coupled to the support shaft 640. A support ring 714 is provided at the mounting sleeve 704, on which a driving surface 706 is formed, that is engaged by a distal end of a biasing element 708, which is arranged as a coil spring 710, for instance. At its proximal end, the biasing element 708 rests on a pressure surface 718 of a retaining piece 712. The retaining piece 712 also comprises a limit stop surface 720 for abutment with the housing 622. By way of example, the holder 712 may be coupled to the housing section 784 of housing 622 via a thread 722. In this way, the retaining piece 712 defines an axial reference or limit stop for the pretensioning element 708 of the preloading unit 702. The preloading unit 702 pushes the support shaft 640 towards the distal end of the 614 instrument shaft and, consequently, via the spacer 658 towards the distal end element 646.

The locating sleeve 704 further comprises a rotary position lock 724 arranged as a recess which cooperates with a rotary position lock 798 in the form of a lug on the housing 622.

The ocular assembly 732 is mounted on a carrier 742 via the tube 734. According to the exemplary embodiment shown in FIG. 9, the carrier 742 is formed by a portion of the mounting sleeve 704. In other words, the tube 734 is mounted on the mounting sleeve 704. A retainer cap 752 is used to secure the position, which is coupled to the mounting sleeve 704 via a thread 754. The retainer 752 comprises a pressure surface 756 that engages a driving collar 758 of the tube 734 in order to fixedly attach the tube 734 to the carrier 742.

The preloading unit 760 comprises a biasing element 766 that is arranged as a coil spring 768, for example. The pretensioning element 766 extends between a connecting piece 764 and the tube 734. A driving collar 770 is formed at the connecting piece 764. The connecting piece 764 is coupled to the rod lens 694. Via the driving collar 770, the connecting piece 764 can transmit a distally directed preloading force to the rod lens assembly 690. Furthermore, the connecting piece 764 comprises a limit stop surface 772 for a distal end of the 766 biasing element. A limit stop face 776 for a proximal end of the biasing element 766 is formed at the tube 734. The biasing element 766 urges the erod lens assembly 90 towards the distal end, i.e. towards the objective lens assembly 650. Further, the biasing element 766 forces the ocular assembly 732 towards a proximal limit stop that is formed by the pressure surface 756 and the driving collar 758.

A difference between the embodiment illustrated in FIGS. 3 to 5 and the embodiment illustrated in FIGS. 8 and 9 is that the ocular assembly 732 is force-fitted against a proximal limit stop by the biasing element 708. However, the ocular assembly 132 (cf. FIG. 3 and FIG. 5) is fixedly attached (both proximally and distally fixed) to the mounting sleeve 104 via the clamping piece 144.

According to the embodiment illustrated in FIG. 9, the ocular assembly 732 may generally be moved distally relative to the mounting sleeve 704, although a force applied by the preloading unit 760 has to be surmounted to this end.

Both in accordance with the embodiment illustrated in FIGS. 3 and 5 and with the embodiment illustrated in FIG. 9, the mounting sleeves 104, 704 are arranged axially displaceable at the housing 22, 622.

What is claimed is:
1. An observation instrument, comprising:
a longitudinally extending instrument shaft having a distal end and a proximal end,
a support shaft arranged in the instrument shaft and having a distal end and a proximal end, and
an optical arrangement at least partially disposed in the instrument shaft,
wherein the optical arrangement comprises at least one optical component that is arranged in the support shaft,
wherein the support shaft extends beyond the proximal end of the instrument shaft so that the proximal end of the support shaft is proximal relative to the proximal end of the instrument shaft,
wherein the support shaft is axially slidably supported in the instrument shaft,
wherein the support shaft is distally preloaded in the instrument shaft by a biasing element that is arranged proximally to the proximal end of the instrument shaft,
wherein the biasing element is a spring element, and
wherein the support shaft extends from the distal end of the instrument shaft to the proximal end of the instrument shaft.
2. The observation instrument according to claim 1, further comprising a distal end element that is fixedly connected to the instrument shaft,
wherein in the instrument shaft, the support shaft is axially preloaded against the distal end element.
3. The observation instrument according to claim 2, further comprising a spacer that is arranged between the support shaft and the distal end element.
4. The observation instrument according to claim 3, wherein the optical arrangement comprises an objective lens assembly, and
wherein the spacer defines a distance between the objective lens assembly and the distal end element.
5. The observation instrument according claim 1, further comprising a head piece that is provided with a housing, wherein the support shaft extends into the housing of the head piece.
6. The observation instrument according to claim 1, further comprising a distal driving surface that is coupled to the support shaft,
wherein the biasing element is disposed between a proximal pressure surface and the distal driving surface.
7. The observation instrument according to claim 1, wherein the biasing element surrounds an observation beam path of the observation instrument.
8. The observation instrument according to claim 1, wherein the biasing element is arranged as a compression spring.
9. The observation instrument according to claim 1, wherein at least a section of the optical arrangement in the support shaft is preloaded distally relative to the support shaft.
10. The observation instrument according to claim 9, wherein the optical arrangement is axially slidably accommodated in the support shaft and preloaded distally by a second biasing element.
11. The observation instrument according to claim 10, wherein the second biasing element is coupled to the at least one optical component, and
wherein the second biasing element preloads the at least one optical component distally relative to the support shaft.
12. The observation instrument according to claim 10, wherein the optical arrangement further comprises an ocular assembly arranged proximal of the support shaft, and
wherein the second biasing element is supported at its proximal end at the ocular assembly.
13. The observation instrument according to claim 1, further comprising an intermediate shaft that is arranged between the instrument shaft and the support shaft, and
wherein the intermediate shaft surrounds the support shaft.
14. The observation instrument according to claim 13, wherein the intermediate shaft is at the distal end fixedly attached to the instrument shaft.
15. The observation instrument according to claim 14, further comprising a distal end element that is arranged in the intermediate shaft.
16. The observation instrument according to claim 13, wherein the intermediate shaft seals the support shaft and the optical arrangement arranged therein.
17. An endoscope, comprising:
an instrument shaft having a distal end and a proximal end,
a support shaft arranged in the instrument shaft and having a distal end and a proximal end, and
an optical arrangement at least sectionally arranged in the instrument shaft, wherein the optical arrangement comprises at least one optical component that is arranged in the support shaft, wherein the support shaft extends beyond the proximal end of the instrument shaft so that the proximal end of the support shaft is proximal relative to the proximal end of the instrument shaft, wherein the support shaft is axially slidably supported in the instrument shaft, wherein the support shaft is distally preloaded in the instrument shaft by a biasing element that is arranged proximally to the proximal end of the instrument shaft, wherein the biasing element is a spring element, wherein at least a section of the optical arrangement in the support shaft is preloaded distally relative to the support shaft, and wherein the support shaft extends from the distal end of the instrument shaft to the proximal end of the instrument shaft.

18. An endoscopic observation instrument, comprising:
an instrument shaft having a distal end and a proximal end,
a support shaft arranged in the instrument shaft and having a distal end and a proximal end,
an intermediate shaft that is arranged between the instrument shaft and the support shaft, and
an optical arrangement at least sectionally arranged in the support shaft and in the intermediate shaft and the instrument shaft, wherein the optical arrangement comprises at least one optical component that is arranged in the support shaft, wherein the support shaft extends beyond the proximal end of the instrument shaft so that the proximal end of the support shaft is proximal relative to the proximal end of the instrument shaft, wherein the support shaft is axially slidably supported in the instrument shaft, wherein the support shaft is distally preloaded in the intermediate shaft by a biasing element that is arranged proximally to the proximal end of the instrument shaft, wherein the biasing element is a spring element, wherein the optical arrangement in the support shaft is at least sectionally preloaded distally relative to the support shaft, wherein the intermediate shaft seals the support shaft and the optical arrangement arranged therein, and wherein the support shaft extends from the distal end of the instrument shaft to the proximal end of the instrument shaft.

\* \* \* \* \*